US008399011B1

(12) United States Patent
Wong et al.

(10) Patent No.: US 8,399,011 B1
(45) Date of Patent: Mar. 19, 2013

(54) ORAL PARTICLE COMPOSITIONS CONTAINING A CORE AND AN ACID-SOLUBLE COAT

(75) Inventors: David Wong, Milpitas, CA (US); James A Lee, San Francisco, CA (US)

(73) Assignee: Magnifica Inc., Fremont, CA (US)

( * ) Notice: Subject to any disclaimer, the term of this patent is extended or adjusted under 35 U.S.C. 154(b) by 0 days.

(21) Appl. No.: 13/571,585

(22) Filed: Aug. 10, 2012

(51) Int. Cl.
*A61F 2/00* (2006.01)
*A61K 9/20* (2006.01)
*A61K 9/14* (2006.01)
*A61K 9/16* (2006.01)

(52) U.S. Cl. ......... 424/424; 424/464; 424/489; 424/490

(58) Field of Classification Search ............... None
See application file for complete search history.

(56) References Cited

U.S. PATENT DOCUMENTS

| 8,202,456 B2 | 6/2012 | Nakashima et al. |
| 2006/0013876 A1 | 1/2006 | Lohray et al. |
| 2006/0269751 A1* | 11/2006 | Winstead et al. ............. 428/403 |
| 2009/0148480 A1 | 6/2009 | Isshiki et al. |
| 2009/0186082 A1* | 7/2009 | Li et al. ................ 424/472 |

FOREIGN PATENT DOCUMENTS

| EP | 2090298 | * | 8/2009 |
| WO | PCT/JP2007/071919 | | 11/2007 |
| WO | WO 2012/030927 | * | 8/2012 |

OTHER PUBLICATIONS

Leopold et al. "Eudragit@ E as Coating Material for the pH-Controlled Drug Release in the Topical Treatment of Inflammatory Bowel Disease (IBD)" Journal of Drug Targeting, 1998. vol. 6, No. 2, pp. 85-89.*

* cited by examiner

*Primary Examiner* — Robert A Wax
*Assistant Examiner* — Danah Al-Awadi

(57) ABSTRACT

The present invention relates to an oral particle composition as an ingredient in an extended-release tablet formulation, comprising a core and a coat, wherein the coat is acid-soluble.

8 Claims, No Drawings

ORAL PARTICLE COMPOSITIONS CONTAINING A CORE AND AN ACID-SOLUBLE COAT

TECHNICAL FIELD

The present invention relates to an oral particle composition as an ingredient in an extended-release tablet formulation, comprising a core and a coat.

BACKGROUND OF THE INVENTION

Oral extended-release solid dosage forms for drug substances are highly desired. Hydrogel tablets made of a hydrogel polymer form a viscous layer at tablet surface during dissolution. The viscous layer retards the drug release from the tablet matrix. The manufacturing process usually is simple and straight-forward, no tedious functional coating process is needed. However, specific excipients (i.e. inactive ingredients) are required to achieve the desired in vivo performances. For instance, U.S. Pat. App. Pub. No. 20090011019 teaches specific excipient is needed for increasing the residence time of the composition disclosed in the gastro-intestinal tract. U.S. Pat. App. Pub. No. 20100285114 teaches the presence of a rate controlling polymer in a drug particle composition to achieve extended release.

Excipients available include but not limited to solubilizing agents, swelling agents, swell-controlling agents, gas generating materials, diluents, binders, disintegrants, lubricants, anti-sticking agents, and glidiants etc.

Excipients usually exist as a single chemical entity. Examples include but not limited to microcrystalline cellulose, hydroxypropyl methylcellulose, polyethylene oxide, polyvinyl pyrrolidone, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, zinc stearate, polyethylene glycol, glyceryl behenate, mineral oil, sodium stearyl fumarate, stearic acid, silicon dioxide; magnesium trisilicate, powdered cellulose, starch, talc and tribasic calcium phosphate, calcium silicate, magnesium silicate, colloidal silicon dioxide, hydrogenated vegetable oil and talc.

While excipients can also be a combination of two or more chemical entities. U.S. Pat. No. 6,391,352 teaches a starch/gum based ingredient for use in food products. U.S. Pat. No. 7,998,505 teaches a "microcrystalline cellulose containing material" consists of microcrystalline cellulose co-processed with carboxymethyl cellulose. U.S. Pat. No. 7,776,358 teaches a matrix material co-processed calcium phosphate and fatty acid wax. U.S. Pat. No. 5,747,067 teaches particulate pharmaceutical tablet excipient compositions comprising co-processed microcrystalline cellulose and particulate USP calcium carbonate. PCT/JP2007/071919 teaches an excipient and an enteric coating agent granulated while spraying a solution or suspension of a pharmaceutical component, thereby producing a granule A. The granule A is mixed with a mixture B which contains a hydrogel-forming substance, and the resulting mixture is shaped into a tablet. EP2090298 teaches a method comprises mixing (1) a granulated product A obtained by granulating an excipient and an enteric coating agent while spraying thereon with a solution or a suspension containing an orally administrable medicinal component, with (2) a composition B containing a hydrogel-forming substance; and then compressing the resulting mixture into a tablet. The chemical entities in these "combo excipients" are evenly distributed over the particle matrix. While the claimed matter in this application is a particle containing a core and an acid-soluble polymer, which may allow a bigger flexibility in the excipient selection for hydrogel tablet development.

BRIEF SUMMARY OF THE INVENTION

The inventor has found a simple method to develop an oral particle composition as an ingredient in an extended-release tablet formulation, comprising (1) a core, and (2) a coat, and wherein the coat is an acid-erodible coat.

According, in one aspect the present invention relates to an oral particle composition comprising a core and an acid-erodible coat. Such oral particle erodes partly or completely in acidic media, including stomach juice. The oral particles are further blended with a drug, a hydrogel polymer and different excipients, compressed to form an extended-release tablet. The tablet may also be a gastric retentive tablet. The tablet composition is optionally coated with a film for cosmetic or other purposes.

In a further aspect, the invention relates to a method for preparing a particle comprising a core and an acid-erodible coat, wherein the coating is performed with a fluid-bed or a vertical granulator.

DETAILED DESCRIPTION OF THE INVENTION

Definitions

As used herein, the term "drug" means a compound intended for use in diagnosis, cure, mitigation, treatment, or prevention of disease in man or other animals. The terms drugs, therapeutics, actives, active ingredient and biological active are inter-changeable.

"Optional" or "optionally" means that the subsequently described circumstance may or may not occur, so that the description includes instances where the circumstance occurs and instances where it does not.

Singular forms included in the claims such as "a", "an" and "the" include the plural reference unless expressly stated or the context clearly indicates otherwise.

By "pharmaceutically acceptable" is meant a carrier comprised of a material that is not biologically or otherwise undesirable.

In the present context, the term "hydrogel polymer" refers to water-soluble polymer with swelling properties. Examples include but not limited to methyl cellulose, hydroxymethyl cellulose, polyvinyl pyrrolidone, hydroxyethyl cellulose, hydroxypropyl cellulose, hydroxypropyl methylcellulose, polyethylene oxides, gums, carbomer, acrylate polymers and methacrylate polymers.

The term "acid-erodible coat" refers to a coat eroding in an acid.

The term "core" refers to the uncoated particle consisting essentially of one substance.

The term "enteric core" refers to the uncoated particle comprising an enteric polymer.

The Invention

The present invention provides an oral particle composition and methods for preparing such compositions. The oral particle compositions are blended with other ingredients and compressed to form a tablet, and the oral particle compositions may have one or more of the following characteristics: (1) eroding in acidic medium, and (2) altering the dissolution profiles of a hydrogel tablet.

Accordingly, this invention provides an oral particle composition comprising a core and an acid-erodible enteric coat. Such oral particle erodes partly or completely in acidic media, including stomach juice. The oral particles are further blended with a drug, a hydrogel polymer and different excipients, compressed to form an extended-release tablet. The tablet composition is optionally coated with a film for cosmetic or other purposes.

Coating "particle cores" can be performed with a fluid bed, a vertical granulator, a planetary mixer or equivalent equipments. Particle core is first placed in the chamber, and sprayed with an acid-soluble coating solution or suspension. The coating solution or suspension contains large amount of an acid-soluble substance to ensure the erodible feature of the coated-particle in the stomach juice.

An oral tablet composition according to the present invention can be obtained by (1) blending and then (2) compressing the particles with a drug, a hydrogel polymer and other excipients. The tablet is an extended-release tablet. The tablet can be optionally film-coated for functional or cosmetic purposes. The functional purposes of the film include moisture-barrier, extended-release, delayed-release, taste-masking etc.

In one embodiment, the oral particle composition comprises a core and an acid-soluble coat; wherein the core is a water-soluble excipient, wherein the coat comprises an acid-soluble polymer and excipients. The particle contains no drug; the particles are further blended with a drug, a hydrogel polymer, and different excipients, compressed to form an extended-release tablet. The tablet composition is optionally coated with a film for cosmetic or other purposes. A wide variety of drugs can be used in conjunction with the present embodiment. (See paragraph [035]-paragraph [037]) Examples of other materials can be found in paragraphs [014], [032]-[034] and [038]-[048].

In another embodiment, the oral particle composition comprises an enteric core and an acid-soluble coat; wherein the coat comprises an acid-soluble polymer and excipients. The particle contains no drug; the particles are further blended with a drug, a hydrogel polymer, and different excipients, compressed to form an extended-release tablet. The tablet composition is optionally coated with a film for cosmetic or other purposes. A wide variety of drugs can be used in conjunction with the present embodiment. (See paragraph [035]-paragraph [037]) Examples of other materials can be found in paragraphs [014], [032]-[034] and [038]-[048].

In a further embodiment, an oral particle composition comprises a core and an acid-soluble coat; wherein the core is a calcium salt particle, wherein the acid-soluble coat comprises amino methacrylate copolymer and excipients. This oral particle is blended with a drug, a hydrogel polymer, and excipients; and then compressed into an extended release tablet. A wide variety of drugs can be used in conjunction with the present embodiment. (See paragraph [035]-paragraph [037]) Examples of other materials can be found in paragraphs [014], [032]-[034] and [038]-[048].

The preferred calcium salts are phosphates, sulfates, and carbonates.

In a preferred embodiment, the oral particle composition comprises an enteric core and an acid-soluble coat, wherein the particle contains no drug, wherein the enteric core comprises a methacrylic acid copolymer; and wherein the acid-soluble coat comprises an amino methacrylate copolymer, wherein the oral pharmaceutical particle is blended with a drug, carbomer, and excipients, and compressed to form a extended-release tablet. The drug is selected from the group consisting of a cholesterol lowering agent, a glucose lowering agent, a blood pressure lowering agent, triglyceride lowering agent and combinations thereof. The preferred drug is selected from the group consisting of lorcaserin hydrochloride, niacin, atorvastatin calcium, fluvastatin sodium, lovastatin, pravastatin sodium, simvastatin, rosuvastatin calcium, cholestyramine, colesevelam hydrochloride, fenofibrate, gemfibrozil, ezetimibe, glipizide, glyburide, glimepiride, repaglinide, nateglinide, sitagliptin phosphate, saxagliptin monohydrate, metformin hydrochloride, pioglitazone hydrochloride, rosiglitazone maleate, miglitol, acarbose, pramlintide acetate, glucagon, insulin, aspirin, captopril, lisinopril, Hydrochlorothiazide, ramipril, losartan potassium, olmesartan medoxomil, valsartan, metoprolol tartrate, metoprolol succinate, nadolol, bendroflumethiazide, penbutolol sulfate, amlodipine besylate and combinations thereof. The most preferred drug is selected from the group consisting of niacin, lorcaserin hydrochloride, fenofibrate, and combinations thereof.

In another preferred embodiment, the oral pharmaceutical particle comprises a core and an acid-soluble coat; wherein the core comprises dicalcium phosphate dihydrate, wherein the acid-soluble coat comprises amino methacrylate copolymer and excipients, wherein the oral pharmaceutical particle is blended with a drug, carbomer, and excipients, and compressed to form an extended-release tablet. The drug is selected from the group consisting of a cholesterol lowering agent, a glucose lowering agent, a blood pressure lowering agent, triglyceride lowering agent and combinations thereof. The preferred drug is selected from the group consisting of lorcaserin hydrochloride, niacin, atorvastatin calcium, fluvastatin sodium, lovastatin, pravastatin sodium, simvastatin, rosuvastatin calcium, cholestyramine, colesevelam hydrochloride, fenofibrate, gemfibrozil, ezetimibe, glipizide, glyburide, glimepiride, repaglinide, nateglinide, sitagliptin phosphate, saxagliptin monohydrate, metformin hydrochloride, pioglitazone hydrochloride, rosiglitazone maleate, miglitol, acarbose, pramlintide acetate, glucagon, insulin, aspirin, captopril, lisinopril, Hydrochlorothiazide, ramipril, losartan potassium, olmesartan medoxomil, valsartan, metoprolol tartrate, metoprolol succinate, nadolol, bendroflumethiazide, penbutolol sulfate, amlodipine besylate and combinations thereof. The most preferred drug is selected from the group consisting of niacin, lorcaserin hydrochloride and fenofibrate combinations thereof.

In a preferred embodiment, the oral particle composition comprises an enteric core and an acid-soluble coat, wherein the particle contains no drug, wherein the enteric core comprises a methacrylic acid copolymer; and wherein the acid-soluble coat comprises an amino methacrylate copolymer, wherein the oral pharmaceutical particle is blended with a drug, polyethylene oxide, and excipients, and compressed to form a extended-release tablet. The drug is selected from the group consisting of a cholesterol lowering agent, a glucose lowering agent, a blood pressure lowering agent, triglyceride lowering agent and combinations thereof. The preferred drug is selected from the group consisting of lorcaserin hydrochloride, niacin, atorvastatin calcium, fluvastatin sodium, lovastatin, pravastatin sodium, simvastatin, rosuvastatin calcium, cholestyramine, colesevelam hydrochloride, fenofibrate, gemfibrozil, ezetimibe, glipizide, glyburide, glimepiride, repaglinide, nateglinide, sitagliptin phosphate, saxagliptin monohydrate, metformin hydrochloride, pioglitazone hydrochloride, rosiglitazone maleate, miglitol, acarbose, pramlintide acetate, glucagon, insulin, aspirin, captopril, lisinopril, Hydrochlorothiazide, ramipril, losartan potassium, olmesartan medoxomil, valsartan, metoprolol tartrate, metoprolol succinate, nadolol, bendroflumethiazide, penbutolol sulfate, amlodipine besylate and combinations thereof. The most preferred drug is selected from the group consisting of niacin, lorcaserin hydrochloride, fenofibrate, and combinations thereof.

In the present invention, the particle is intended to be blended with other ingredients and compressed to form extended-release tablet. Thus, in another embodiment, the oral pharmaceutical extended-release tablet composition comprises a particle comprising an enteric core and an acid-soluble coat, a drug, carbomer and excipients. The enteric core comprises a methacrylic acid copolymer; and the acid-soluble coat comprises an amino methacrylate copolymer. The drug is selected from the group consisting of a cholesterol lowering agent, a glucose lowering agent, a blood pressure lowering agent, a triglyceride lowering agent and combinations thereof. The preferred drug is selected from the group consisting of lorcaserin hydrochloride, niacin, atorvastatin calcium, fluvastatin sodium, lovastatin, pravastatin sodium, simvastatin, rosuvastatin calcium, cholestyramine, colesevelam hydrochloride, fenofibrate, gemfibrozil, ezetimibe, glipizide, glyburide, glimepiride, repaglinide, nateglinide, sitagliptin phosphate, saxagliptin monohydrate, metformin hydrochloride, pioglitazone hydrochloride, rosiglitazone maleate, miglitol, acarbose, pramlintide acetate, glucagon, insulin, aspirin, captopril, lisinopril, Hydrochlorothiazide, ramipril, losartan potassium, olmesartan medoxomil, valsartan, metoprolol tartrate, metoprolol succinate, nadolol, bendroflumethiazide, penbutolol sulfate, amlodipine besylate and combinations thereof. The most preferred drug is selected from the group consisting of niacin, lorcaserin hydrochloride and fenofibrate combinations thereof.

The oral pharmaceutical extended release tablet according to paragraph [030] may further comprise a particle comprising a core and an acid-soluble coat; wherein the core comprises dicalcium phosphate dihydrate, wherein the acid-soluble coat comprises amino methacrylate copolymer and excipients.

The manufacturing process is divided into particle core coating, blending and compression. The coating on the "particle core" is carried out in a known manner, for example, by the fluidized bed coating method or granulator coating method through spraying a dispersion or solution of a coating base in water or an organic solvent onto the core. Details for fluidized bed coating method can be found in U.S. Pat. No. 5,236,503 while details for granulator coating is described in U.S. Patent Application No. 20100239681. Blending of the particle with the drug and other excipients can be done with any standard pharmaceutical blender, such as V-shaped blender. Finally, the blend can be compressed into an oral tablet using conventional tableting equipment using standard techniques. Techniques for making tablets are described in Remington's Pharmaceutical Sciences, (Arthur Osol, editor), 1553-1593 (1980).

In some embodiments, the core comprises a water-soluble material or a calcium salt. Examples of water-soluble excipients for the core include hydroxyalkyl celluloses such as hydroxypropyl cellulose, hydroxypropylmethyl cellulose (2208, 2906 and 2910) or hydroxyethyl cellulose; polyvinyl derivatives such as povidone, crospovidone or polyvinyl alcohol; polyethylene oxides; methyl cellulose; gelatin; polysaccharides such as pregelatinized starch, partially pregelatinized starch, pullulan, dextrin, sodium alginate or gum Arabic, polyethylene glycols; sugars such as lactose, saccharose, trehalose or glucose; and sugar alcohols such as mannitol, xylitol, sorbitol, erythritol or maltitol. Among these, sugars or sugar alcohols are preferred.

Enteric core comprises an enteric polymer. Enteric polymer is a polymer soluble at pH 5.5 or above. Examples of enteric polymer include but not limited to methacrylic acid copolymer, Type A, methacrylic acid copolymer, Type B, hydroxypropyl methylcellulose acetate succinate (also known as hypromellose acetate succinate), cellulose acetate phthalate, hydroxypropyl methyl cellulose phthalate, polyvinyl acetate phthalate, alginic acid, and sodium alginate.

Acid soluble polymer is a polymer soluble in gastric fluid up to pH 5.0. Example of an acid-soluble polymer is but not limited to amino methacrylate copolymer—NF A wide variety of drugs can be used in conjunction with the present invention. Examples of such drugs include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenyloin, meprobamate and nitrezepam), vasodilators (e.g., nifedipine, papaverine, diltiazem and nicardipine), anti-tussive agents and expectorants (e.g., codeine phosphate), anti-asthmatics (e.g. theophylline), antacids, anti-spasmodics (e.g., atropine, scopolamine), antidiabetics (e.g., insulin), diuretics (e.g., ethacrynic acid, bendrofluazide), anti-hypotensives (e.g., propranolol, clonidine), antihypertensives (e.g., clonidine, methyldopa), bronchodilators (e.g., albuterol), steroids (e.g., hydrocortisone, triamcinolone, prednisone), antibiotics (e.g., tetracycline), antihemorrhoidals, hypnotics, psycho-tropics, antidiarrheals, mucolytics, sedatives, decongestants, laxatives, vitamins, stimulants (including appetite suppressants such as phenylpropanolamine), as well as salts, hydrates, and solvates of the same. The above list is not meant to be exclusive.

In certain embodiments, the drug comprises cholesterol lowering agents, glucose lowering agents, triglyceride lowering agent and blood pressure lowering agents, mixtures of any of the foregoing, and the like. Examples of cholesterol lowering agents include but not limited to statins, niacin, bile-acid resins, fibric acid derivatives and cholesterol absorption inhibitors. Examples of glucose lowering agents include but not limited to biguaride, metformin, sulfonylureas, non-sulfonylurea, glucosidase inhibitor and DPP-IV inhibitor. Examples of triglyceride lowering agents include but not limited to fenofibrate and gemfibrozil. Examples of blood pressure lowering agents include but not limited to diuretics, beta-blockers, ACE inhibitors, angiotensin antagonists, calcium channel blockers, alpha-blockers, alpha-beta-blockers, nervous system inhibitors and vasodilators.

In particular embodiments, the drug comprises lorcaserin hydrochloride, niacin, atorvastatin calcium, fluvastatin sodium, lovastatin, pravastatin sodium, simvastatin, rosuvastatin calcium, cholestyramine, colesevelam hydrochloride, fenofibrate, gemfibrozil, ezetimibe, glipizide, glyburide, glimepiride, repaglinide, nateglinide, sitagliptin phosphate, saxagliptin monohydrate, metformin hydrochloride, pioglitazone hydrochloride, rosiglitazone maleate, miglitol, acarbose, pramlintide acetate, glucagon, insulin, aspirin, captopril, lisinopril, Hydrochlorothiazide, ramipril, losartan potassium, olmesartan medoxomil, valsartan, metoprolol tartrate, metoprolol succinate, nadolol, bendroflumethiazide, penbutolol sulfate, amlodipine besylate, the derivatives of these drugs, and combinations thereof.

The amount of excipient employed will depend upon how much active agent is to be used. One excipient can perform multi-functionally. Examples of excipients include but not limited to retarding agent, binder, filler, diluents, lubricant or a mixture thereof.

Retarding agent is any substance retards the drug release to produce the controlled-release effect. Examples of retarding agent include but not limited to wax, hydrogel polymer, and many other water-insoluble materials. In the invention, the hydrogel polymer is the key retarding agent. (See paragraph [014])

Binders include, but not limited to, starches such as potato starch, wheat starch, corn starch; microcrystalline cellulose; celluloses such as hydroxypropyl cellulose, hydroxyethyl cellulose, hydroxypropyl methylcellulose, ethyl cellulose, sodium carboxy methylcellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, combinations thereof and other materials known to one of ordinary skill in the art and mixtures thereof.

Fillers or diluents, which include, but not limited to sugar, dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, and the like can be used.

Lubricants may be selected from, but are not limited to, those conventionally known in the art such as magnesium, aluminum or calcium or zinc stearate, polyethylene glycol, glyceryl behenate, mineral oil, sodium stearyl fumarate, stearic acid, hydrogenated vegetable oil and talc.

Glidants include, but not limited to, silicon dioxide; magnesium trisilicate, powdered cellulose, starch, talc and tribasic calcium phosphate, calcium silicate, magnesium silicate, colloidal silicon dioxide, silicon hydrogel and other materials known to one of ordinary skill in the art.

The pharmaceutical dosage form of the invention can optionally have one or more coatings such as moisture-barrier film coating, sugar coating, enteric coating, bioadhesive coating and other coatings known in the art. These coatings help pharmaceutical formulations to release the drug at the required site of action. In one example, the additional coating prevents the dosage from contacting the mouth or esophagus. In another example, the additional coating remains intact until reaching the small intestine or colon (e.g., an enteric coating).

These coating layers comprises one or more excipients selected from the group comprising coating agents, plasticizers, channeling agents, opacifiers, taste-masking agents, fillers, polishing agents, coloring agents, anti-tacking agents and the like.

Coating agents which are useful in the coating process, include, but not limited to, polysaccharides such as maltodextrin, alkyl celluloses such as methyl or ethyl cellulose, cellulose acetate, hydroxyalkylcelluloses (e.g. hydroxypropylcellulose or hydroxypropylmethylcelluloses); polyvinylpyrrolidone, acacia, corn, sucrose, gelatin, shellac, cellulose acetate pthalate, lipids, synthetic resins, acrylic polymers, OPADRY® coating systems, polyvinyl alcohol (PVA), copolymers of vinylpyrrolidone and vinyl acetate (e.g. marketed under the brand name of PLASDONE®) and polymers based on methacrylic acid such as those marketed under the brand name of EUDRAGIT®. These may be applied from aqueous or non-aqueous systems or combinations of aqueous and non-aqueous systems as appropriate.

Additives can be included along with the film formers to obtain satisfactory films. These additives can include plasticizers such as dibutyl phthalate, triethyl citrate, polyethylene glycol (PEG) and the like, channeling agents such as surfactants, short-chain water-soluble polymers, salts and the like, antitacking agents such as talc, stearic acid, magnesium stearate and colloidal silicon dioxide and the like, fillers such as talc, precipitated calcium carbonate, polishing agents such as Beeswax, carnauba wax, synthetic chlorinated wax and opacifying agents such as titanium dioxide and the like. All these excipients can be used at levels well known to the persons skilled in the art.

EXAMPLES OF INVENTION

The foregoing examples are illustrative embodiments of the invention and are merely exemplary. A person skilled in the art may make variations and modifications without deviating from the spirit and scope of the invention. All such modifications and variations are intended to be included within the scope of the invention.

Example 1

Lactose is placed in a chamber. Amino methacrylate copolymer—NF, polyethylene glycol, talc and colloidal silicon dioxide suspension is prepared and sprayed onto the lactose. The coated lactose is dried at 50 deg. C.

Example 2

The coated lactose in Example 1 is blend with simvastatin, polyethylene oxide, microcrystalline cellulose, carbomer, talc and magnesium stearate and compressed into a tablet.

Example 3

The coated lactose in Example 1 is blend with atorvastatin calcium, polyethylene oxide, microcrystalline cellulose, polyethylene oxide, talc and magnesium stearate and compressed into a tablet.

Example 4

Methacrylic acid copolymer is passed through a 40 mesh screen and a 80 mesh screen in series. The portion on the 80 mesh screen is used for the study. The screened methacrylic acid copolymer is placed in a chamber. Amino methacrylate copolymer—NF, polyethylene glycol, talc and colloidal silicon dioxide suspension is prepared and sprayed onto the enteric polymer. The coated lactose is dried at 50 deg. C.

Example 5

The coated particle in Example 4 is blend with simvastatin, polyethylene oxide, microcrystalline cellulose, talc and magnesium stearate and compressed into a tablet.

Example 6

The coated particle in Example 4 is blend with atorvastatin, carbomer, microcrystalline cellulose, talc and magnesium stearate and compressed into a tablet.

Example 7

Dicalcium Phosphate Dihydrate, Unmilled, is passed through a 40 mesh screen and a 80 mesh screen in series. The portion on the 80 mesh screen is used for the study. The screened methacrylic acid copolymer is placed in a chamber. Amino methacrylate copolymer—NF, polyethylene glycol, talc and colloidal silicon dioxide suspension is prepared and sprayed onto the particles. The coated lactose is dried at 50 deg. C.

Example 8

The coated particle in Example 7 is passed through a 18 mesh screen, the portion through the 18 mesh screen is blend with lorcaserin hydrochloride, polyethylene oxide, microcrystalline cellulose, hydroxypropyl methylcellulose, talc and magnesium stearate and compressed into a tablet.

Example 9

The coated particle in Example 7 is passed through a 18 mesh screen, the portion through the 18 mesh screen is blend with lorcaserin hydrochloride, fenofibrate, polyethylene oxide, microcrystalline cellulose, hydroxypropyl methylcellulose, talc and magnesium stearate and compressed into a tablet.

We claim:

1. An extended-release tablet comprising: (1) an oral pharmaceutical particle comprising an enteric core and an acid-soluble coat, wherein the particle contains no drug, wherein the enteric core comprises a methacrylic acid copolymer; and wherein the acid-soluble coat comprises an amino methacrylate copolymer which is blended and then compressed with (2) a drug, (3) carbomer, and (4) excipients to form an extended release tablet, (2) a drug, (3) carbomer, and (4) excipients.

2. The extended-release tablet according to claim 1, wherein the drug is selected from the group consisting of a cholesterol lowering agent, a glucose lowering agent, a blood pressure lowering agent, a triglyceride lowering agent and combinations thereof.

3. The extended-release tablet according to claim 1, wherein the drug is selected from the group consisting of lorcaserin hydrochloride, niacin, atorvastatin calcium, fluvastatin sodium, lovastatin, pravastatin sodium, simvastatin, rosuvastatin calcium, cholestyramine, colesevelam hydrochloride, fenofibrate, gemfibrozil, ezetimibe, glipizide, glyburide, glimepiride, repaglinide, nateglinide, sitagliptin phosphate, saxagliptin monohydrate, metformin hydrochloride, pioglitazone hydrochloride, rosiglitazone maleate, miglitol, acarbose, pramlintide acetate, glucagon, insulin, aspirin, captopril, lisinopril, Hydrochlorothiazide, ramipril, losartan potassium, olmesartan medoxomil, valsartan, metoprolol tartrate, metoprolol succinate, nadolol, bendroflumethiazide, penbutolol sulfate, amlodipine besylate and combinations thereof.

4. The extended-release tablet according to claim 1, wherein the drug is selected from the group consisting of niacin, lorcaserin hydrochloride and fenofibrate combinations thereof.

5. The extended-release tablet according to claim 1, wherein the drug is selected from the group consisting of niacin, lorcaserin hydrochloride and combinations thereof.

6. The extended-release tablet according to claim 1, wherein the drug is selected from the group consisting of fenofibrate, lorcaserin hydrochloride and combinations thereof.

7. The extended-release tablet according to claim 1, wherein the drug is lorcaserin hydrochloride.

8. An extended-release tablet comprising: (1) an oral pharmaceutical particle comprising an enteric core and an acid-soluble coat, wherein the particle contains no drug, wherein the enteric core comprises a methacrylic acid copolymer; and wherein the acid-soluble coat comprises an amino methacrylate copolymer which is blended and then compressed with (2) a drug, (3) polyethylene oxide, and (4) excipients to form an extended release tablet, (2) a drug, (3) polyethylene oxide and (3) excipients.

* * * * *